US008685184B2

(12) United States Patent
Johnson et al.

(10) Patent No.: US 8,685,184 B2
(45) Date of Patent: *Apr. 1, 2014

(54) SHAPE SETTING A SHAPE MEMORY ALLOY DENTAL ARCH (75) Inventors: Alfred David Johnson, San Leandro, CA (US); Sammel S. Alauddin, Orange, CA (US)

(73) Assignee: Ormco Corporation, Orange, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 13/215,438

(22) Filed: Aug. 23, 2011

(65) Prior Publication Data

US 2012/0048432 A1    Mar. 1, 2012

Related U.S. Application Data (60) Provisional application No. 61/376,608, filed on Aug. 24, 2010.

(51) Int. Cl.
*C22F 1/08*     (2006.01)

(52) U.S. Cl.
USPC .......................................... 148/562; 148/563

(58) Field of Classification Search
USPC ................ 148/562, 563, 402; 72/364; 433/20
See application file for complete search history.

(56) References Cited

U.S. PATENT DOCUMENTS

| 4,919,177 | A  | * | 4/1990 | Homma ........................ 148/563 |
| 5,092,941 | A  | * | 3/1992 | Miura .......................... 148/563 |
| 7,441,888 | B1 | * | 10/2008 | Johnson .......................... 351/41 |
| 7,842,143 | B2 | * | 11/2010 | Johnson et al. ............... 148/562 |
| 8,382,917 | B2 | * | 2/2013 | Johnson ........................ 148/562 |
| 2009/0061378 | A1 | * | 3/2009 | Kim et al. ....................... 433/20 |

* cited by examiner

*Primary Examiner* — Scott Kastler
*Assistant Examiner* — Michael Aboagye
(74) *Attorney, Agent, or Firm* — Wood, Herron & Evans, LLP (57) ABSTRACT Described herein are methods, systems, and apparatus for shape-setting hyperelastic, single-crystal shape memory alloy (SMA) material while preserving the hyperelastic properties of the material. Also described are hyperelastic, single-crystal SMA devices that have been shape set by these methods. In particular, described herein are hyperelastic, single crystal SMA dental archwires and methods of forming them while preserving the hyperelastic properties, e.g., without significant grain boundaries in the crystal structure.

27 Claims, 4 Drawing Sheets

SHAPE SETTING A SHAPE MEMORY ALLOY DENTAL ARCH

CROSS REFERENCE TO RELATED APPLICATIONS

This patent application claims priority to U.S. Provisional Patent Application No. 61/376,608, titled "SHAPE SETTING A SHAPE MEMORY ALLOY DENTAL ARCH," filed on Aug. 24, 2010.

This patent application may be related to U.S. patent application Ser. No. 11/949,663, titled "HYPERELASTIC SHAPE SETTING DEVICES AND FABRICATION METHODS," filed on Dec. 3, 2007, now U.S. Pat. No. 7,842,143. This patent application is herein incorporated by reference in its entirety.

INCORPORATION BY REFERENCE

All publications and patent applications mentioned in this specification are herein incorporated by reference in their entirety the same extent as if each individual publication or patent application was specifically and individually indicated to be incorporated by reference.

FIELD

Described herein are improved and additional methods for shape setting shape memory alloy (SMA) wires, and devices made thereby. The SMA materials described herein may be single crystal SMA materials.

BACKGROUND

In orthodontics, to correct malocclusions, it is a standard procedure to attach individual teeth to a flexible component called an archwire. These are generally of a simple curved shape as illustrated in the FIGS. 1A and 1B. Commercially available archwires are formed of stainless steel or nickel titanium (e.g., Nitinol, aka TiNi or NiTi). Shape memory alloys (SMAs) such as Nitinol are particularly attractive for use as archwires because this material has "super-elastic" properties above characteristic temperatures, in addition to shape memory mechanics upon heating past those temperatures. These characteristic properties arise by virtue of the martensitic transformation that such materials undergo. Unlike strain with traditional dislocations, martensitic transformations (e.g., transformations from an austenite to a martensite configuration) operate by rearrangement of atoms along twin planes in the crystal to accommodate the stress inherently upon the alloy. The end result is completely new crystal structure (martensite) or phase.

Nickel titanium alloys used in orthodontics take full advantage of the superelasticity enabled by this phase change, often accommodating up to 6% full recovery. However, there is significant room for improvement with regard to these materials. For example, severe malocclusions present major force, sliding and super-elastic expectations upon archwires. Additionally, nickel titanium alloy wires express a large stress hysteresis upon straining after the initial elastic properties are consumed. Clinically, this means: 1) forces can often exceed levels of patient comfort; 2) resistance to sliding in brackets is dominated by binding forces between the bracket/wire; and 3) wires take a permanent set or exhibit incomplete recovery upon high straining. Nickel titanium alloys may also exhibit full strain recovery without adequate force upon unloading to efficiently move teeth due to hysteresis growth upon high strain. This graphically manifests as a low tapering unloading curve which may or may not return to zero strain. These mechanical variances often occur from inconsistent annealing or cold working.

When used for orthodontic treatment, archwires are progressed sequentially thru a bracket system ligated to a dental arch. This requires a wire change whenever the size and/or cross sectional form need adjustment. Cases generally begin with small round (e.g. 0.014") wires and complete with large rectangular (e.g. 0.021×0.025") wires (see, e.g., Table 1). Early stage wires are typically round shape memory alloys with superelastic properties. These wires are expected to accommodate large deflections while delivering low constant force. Clinically, this stage of treatment levels and aligns teeth via intrusion/extrusion, rotation, translation and tip. Rectangular cross sections are introduced in each case when torque is required to correct the malocclusion.

TABLE 1

Exemplary Wire Sizes and Geometries

| Size [inches] | Geometry |
|---|---|
| 0.014 | Round |
| 0.016 | Round |
| 0.018 | Round |
| 0.016 × 0.016 | Square |
| 0.014 × 0.025 | Rectangular |
| 0.016 × 0.025 | Rectangular |
| 0.018 × 0.025 | Rectangular |
| 0.019 × 0.025 | Rectangular |
| 0.021 × 0.025 | Rectangular |

For example, upon greater than 2% strain either in tensile or flexure (deflection), typical 0.016" round nickel titanium wires express ~300 MPa loading and ~200 MPa unloading on a standard stress strain curve. This hysteresis may be problematic because there is likely to be a discrepancy of force between clinician installation and wire operation. In addition, the greater hysteresis for SMA's represents a greater likelihood of fatigue. Further, mastication introduces cycling thru the loading and unloading stress plateaus on the material, growing the hysteresis and effectively reducing the biological correction forces. Finally, larger strains introduce greater hysteresis for traditional nickel titanium alloys, thus greater malocclusions are difficult to treat and often introduce permanent sets.

Thus, it would be beneficial to manufacture archwires that address these problems, yet still exhibit some of the beneficial properties of nickel titanium alloys. Described herein are archwires made of "hyperelastic" (rather than simply super-elastic) shape memory alloys that may address many of the problems mentioned above.

As described in detail below, hyperelastic SMA exhibit properties enabling them to undergo large recoverable distortions. Such distortions can be at least an order of magnitude greater than that which could be obtained if the component were made of non-SMA metals and alloys, and nearly an order of magnitude greater than can be obtained with polycrystalline SMA materials.

Examples of hyperelastic SMA include single crystal copper-based shape memory alloys including: CuAlNi, CuNiMn, and CuAlBe. See, e.g., WO2005/108635, filed Nov. 17, 2005, and U.S. Pat. No. 7,842,143. Hyperelastic wires may have a fully recoverable strain exceeding 10 percent; a very small thermomechanical hysteresis; phase transition temperatures ranging from cryogenic to more than 200° C.; low stress-induced-martensite stresses; and low effective sliding friction. These alloys are also biocompatible (see, e.g., Johnson, "Biocompatibility of copper-based single crystal shape memory alloys," Proceedings of the International Conference on Shape Memory and Superelastic Technologies, Shuichi Miyazaki editor, SMST-2007, Tskuba, Japan, December 2007, and US 2009/0187243).

In addition to CuAlNi, CuAlMn and CuAlBe, other alloys are known to be hyperelastic and may be used as described herein. Compositions range from: CuAl(14-14.5)Ni(3-4.5) with CuAl(14.3)Ni(4.5) preferred for dental arches; CuAl(12)Be(0.5); and CuAl(11.5-12.8)Mn(4.5-8) weight percent. Others are being investigated, such as CuAl(12)Ni(4)Mn(2)Ti(1).

Specifically, hyperelastic single crystal SMAs have many advantages over polycrystal SMAs, For example, single crystal SMAs may exhibit greater than 10 percent strain recovery; there is a large gain in performance over the conventional SMA materials made from bulk materials, such as NiTi. Single crystal SMAs may also exhibit true constant force deflection. Unlike polycrystalline materials which reach their strain/stress plateau strength in a gradual fashion and maintain an upward slope when deformed further, hyperelastic SMA materials have a very sharp and clear plateau strain/stress that provides a truly constant stress when deformed up to 10 percent. The stress level at which the plateau occurs depends on the temperature difference between the transformation temperature and the loading temperature. Additionally, some single crystal SMAs exhibiting hyperelasticity, for example CuAlBe, benefit from a second stress plateau which can increase the total recoverable strain to 22 percent.

Single crystal SMAs may also have a very narrow loading-unloading hysteresis. As a result there is substantially the same constant force during both loading (increasing stress) and unloading (decreasing stress). This characteristic may be important for applications where the flexure undergoes repeated cycling, as with archwires.

Further, single crystal SMAs may exhibit recovery which is 100 percent repeatable and complete. One of the drawbacks of polycrystalline SMA materials has always been the "settling" that occurs as the material is cycled back and forth. The settling problem has required that the material be either "trained" as part of the manufacturing process, or designed into the application such that the permanent deformation which occurs over the first several cycles does not adversely affect the function of the device. By comparison, hyperelastic SMA materials do not develop such permanent deformations and therefore significantly simplify the design process into various applications.

Copper-based hyperelastic single crystal SMAs exhibit generally lower stress levels than titanium-based alloys. In fact, because the stress-induced martensite transformation is complete, the stress plateau can be near zero or as large as several hundred megapascals depending on composition and temperature. This adjustable nature of hyperelastic SMAs allows greater versatility in clinical applications.

Unlike NiTi SMAs, which must be conditioned, through a combination of alloying, heat treatment and cold working, to have superelastic properties, single crystal CuAlNi SMA has intrinsic hyperelastic properties: a crystal of CuAlNi may be hyperelastic immediately after being formed as described herein, with no further processing required.

Although single crystal SMAs have been known for several years, to date they have not been successfully used to create archwires, at least in part because it has proven difficult to shape such hyperelastic materials into the archwire form without destroying the single crystal properties by introducing dislocations in the crystal structure. In particular, known fabrication techniques for polycrystalline SMAs and even known methods of fabricating single crystal SMAs are inadequate when forming archwires, particularly those having non-circular cross-sections and/or those pre-bent in the arch shape.

SUMMARY OF THE DISCLOSURE

Described herein are dental archwires formed of hyperelastic shape memory alloys (SMAs), and in particular, dental archwires of single crystal shape memory alloy materials. Also described herein are methods of fabricating, forming, and/or manufacturing dental archwires comprising hyperelastic shape memory alloys such as single crystal shape memory alloys.

In general, the hyperelastic alloys (and particularly the single crystal SMA alloys) described in this disclosure can readily maintain equal loading and unloading stress at very high strains (in some variations greater than 10%). The absence of a true hysteresis provides significant clinical advantages in avoiding fatigue and permanent set. Additionally, the loading/unloading plateau can be independently controlled via alloy composition. Traditional nickel titanium wires rely upon heat treatment and cold work reduction in addition to compositional effects to determine final stress-strain behavior. Cold working of single crystal SMAs would destroy the hyperelastic properties of the SMA, likely disrupting the single crystal structure, and causing it to revert to polycrystalline form. Poor adhesion at crystal grain boundaries, combined with the large shape change associated with stress-induced martensite transformation, causes polycrystalline CuAlNi to be brittle and lacking hyperelastic properties.

The relationship of stress (force) to transformation properties of SMAs generally revolves around the transformation temperatures. Current archwire technology using NiTi shape memory alloys rely on the inherent nature of these materials to exhibit mechanical forces as a function of defined processing. A combination of elemental composition, thermal treatment and physical stress in wire manufacturing establishes the transformation properties, characteristically noted as temperatures ($A_s$, $A_f$, $M_s$, $M_f$). These transformation temperatures define points at which crystal structures (austenite and martensite) start and finish growth upon heating and cooling cycles. Because these crystal structures (phases) carry inherently different mechanical properties, a volume fraction of these phases will exist at any particular temperature and thus establish a distinctive set of mechanical properties for the given conditions. Martensite is soft and ductile while austenite is rigid and elastic. Alloy composition is the most significant factor in defining transformation temperatures, especially with hyperelastic alloys, thus it can be noted in shorthand as:

$$\Delta\text{chemistry} = \Delta A_f = \Delta\text{forces}$$

Orthodontic archwire manufacturers establish forces exerted upon teeth based upon set transformation temperatures, often summarized by $A_f$. Lesser $A_f$ wire exhibits greater stiffness and elasticity, greater $A_f$ wire is softer and more ductile. For these unique alloys, this is graphically represented by the height of loading and/or unloading plateaus in stress-strain, Precise control over this force expression upon teeth is attainable to a greater degree with hyperelastic alloys because these properties are inherently locked into the single crystal. This presents a clear manufacturing advantage over NiTi alloys because successive heat treatments and cold working is not required to control the mechanical properties. Additionally, this provides broad flexibility in product offering to accommodate various clinician and patient needs.

A number of existing patents (Including: U.S. Pat. No. 5,683,245, U.S. Pat. No. 5,474,448; U.S. Pat. No. 5,456,600; U.S. Pat. No. 5,447,432; U.S. Pat. No. 5,395,238; U.S. Pat. No. 5,131,843; and U.S. Pat. No. 5,044,947) to Ormco Corporation describe the use of Cu containing shape memory alloys in orthodontics, including the use of CuNiTi®, as described in U.S. Pat. No. 5,044,947. However, the archwires formed as described herein generally have superior properties even as compared to the polycrystalline SMA archwires described in these references.

For example, described herein are methods of shape-setting a hyperelastic material while preserving the hyperelastic properties of the material, the method comprising: heating a single crystal shape memory alloy material to an annealing temperature ($T_a$); and driving the single crystal shape memory alloy material at the annealing temperature and a shaping form together and into a quenching medium; wherein the heating and driving steps are performed in less than about a minute.

The step of heating may include heating a wire or rod of single crystal shape memory alloy to the annealing temperature. The wire or rod may be a single crystal shape memory alloy of CuAlNi, CuAlMn, CuAlBe, or CuAlNiMnTi. In some variations, the step of heating comprises Joule heating the wire or rod of single crystal shape memory alloy.

The heating portion of the method may be performed quickly. For example, the single crystal SMA may be heated to the annealing temperature within less than about 2 seconds, less than about 1 second, less than about 0.5 seconds, or faster.

The step of driving may generally mean either driving the single crystal shape memory alloy material (at the annealing temperature) against the shaping form, driving the shaping form against the single crystal shape memory alloy material, or driving the two together. The two (or at least the single crystal SMA material) may be quenched by immersing into a quenching medium (e.g., salt water) as part of the same driving step.

For example, the step of driving may include colliding the single crystal shape memory alloy with a shaping form comprising a mandrel. The driving step may be performed by dropping (e.g., dropping the shaping form against the SMA material or vice versa and allowing them both to drop into the quenching medium). In some variations the driving step may be performed by mechanically driving one or both of the SMA material and forming shape. For example, driving may include mechanically accelerating the single crystal shape memory alloy at the annealing temperature and the shaping form against each other and into the quenching medium.

The entire process of heating and driving may be performed in less than a minute, less than 5 seconds, less than 2 seconds, or less than one second. For example, the heating and driving steps may be performed in less than a few (e.g., two) seconds, or less than a (e.g., one) second.

In some variations, the method may be used to form a dental archwire. For example, the step of driving may include forming a dental archwire from the single-crystal shape memory alloy by driving the single crystal shape memory alloy material at the annealing temperature and the shaping form together and into the quenching medium.

Also described herein are methods of shape-setting a hyperelastic material into a dental archwire while preserving the hyperelastic properties of the material, the method comprising: heating a wire of single crystal shape memory alloy material to an annealing temperature ($T_a$); and driving the wire at the annealing temperature and a shaping form together and into a quenching medium to shape-set the wire into an archwire shape; wherein the heating and driving steps are performed in less than five seconds.

As mentioned, the step of heating may include heating a wire, comprising a single crystal shape memory alloy of CuAlNi, CuAlMn, CuAlBe, or CuAlNiMnTi. The heating may be Joule (electric) heating the wire of single crystal shape memory alloy. The heating step may be performed within less than about 0.5 seconds.

The driving step may include driving the wire at the annealing temperature against the shaping form, or driving the shaping form against the wire at the annealing temperature, or driving the two together. In some variations the driving step is driven by gravity, by a mechanical driver (e.g. motor, spring, etc.), pneumatically, or the like.

Also described herein are devices formed by either of these methods. For example, also described herein are hyperelastic dental archwire formed by the method of: heating a wire of single crystal shape memory alloy material to an annealing temperature ($T_a$); and driving the wire at the annealing temperature and a shaping form together and into a quenching medium to shape-set the wire into an archwire shape; wherein the heating and driving steps are performed in less than five seconds, less than 2 seconds, less than 1 second, or the like.

For example, described herein are hyperelastic dental archwire having an elongate, curved length, wherein the hyperelastic dental archwire functions as a single crystal shape memory material, so that it has greater than a 10 percent strain recovery, a constant force deflection, a total recoverable strain up to 22 percent, a very narrow loading-unloading hysteresis recovery which is 100 percent repeatable and complete, and a low sliding friction.

The archwire may have an elongate curved length that is U-shaped. The elongate curved length may have a rectangular cross-section between 0.013×0.018 and 0.020×0.026 inches over at least a portion of its length. In some variations, the elongate curved length has a circular cross-section of diameter 0.013 through 0.026 inches over at least a portion of its length.

As mentioned, the archwire may be a single crystal shape memory material comprising a single crystal of CuAlNi, CuAlMn, CuAlBe, or CuAlNiMnTi.

Also described herein are curved or bent hyperelastic shape memory alloy (SMA) structure that are shape-set into the curved or bent shape, wherein the structure functions as a single crystal SMA having greater than 10 percent strain recovery, constant force deflection, total recoverable strain up to 22 percent, a very narrow loading-unloading hysteresis recovery which is 100 percent repeatable and complete, and a low sliding friction. These curved or bent structure may be formed of a single crystal of CuAlNi, CuAlMn, CuAlBe, or CuAlNiMnTi.

In any of the hyperelastic shape-set structures described herein, the curvature may be substantial. For example, the curvature of the shape-set structure may have an angle or radius of curvature that is greater than about 30 degrees, greater than about 45 degrees, greater than about 60 degrees, greater than about 75 degrees, greater than about 90 degrees, greater than about 135 degrees, greater than about 180 degrees, etc. In some variations, the hyperelastic shape-set structures described herein are shape set into a "bend" in which adjacent regions are substantially straight, but these region are connected by a smaller bend region forming an the device into an angled shape. The angle of the bend region may be any appropriate angle (e.g., greater than 30 degrees, greater than 45 degrees, greater than 60 degrees, greater than 75 degrees, greater than 90 degrees, greater than 135 degrees, greater than 180 degrees, etc.).

The hyperelastic SMA arch wire devices described herein may simplify treatment of malocclusions by combining the functions of different archwires currently required for use during different phases of treatment. For example, standard orthodontic mechanics with NiTi, TMA and stainless steel (SS) wires are designed to take full advantage of particular material properties for a given archwire throughout different phases of the treatment. During the initial phases of treatment, the treatment may require a low force elastic behavior from the wires to align the malocclusive dentition and level the maxillary and mandibular arches. Intermediate phases of treatment may require tip and torque interaction with the brackets with slightly greater forces. Finally, finishing phase mechanics may require fine tuning and individual tooth control. Exemplary material properties of these Cu based single crystal wires could merge much of the initial and intermediate phases, overall reducing treatment time.

In comparison to NiTi and TMA, single crystal, hyperelastic archwires (e.g., CuAlNi wires) may provide improved patient comfort (low force), osteo-compatibility for efficient bone remodeling (constant force which can be precisely set), resistance to permanent set for severe malocclusions (greater superelasticity), clinical ease of use (no hysteresis), resistance to cyclic failure (longer fatigue life) and case efficiency (lower frictionless binding). Because a hyperelastic SMA wire behaves much "smaller" than an equivalently-sized NiTi counterpart (e.g., exerts mechanical forces equivalent to those typically seen in smaller NiTi wires), there is an opportunity to introduce larger rectangular wires (torque) much earlier in the treatment process, effectively merging the use of NiTi and TMA & intermediate phases). For example, a 0.027" round CuAlNi wire exhibits the equivalent flexure force of a 0.018 NiTi wire. Additionally, the greater superelastic range accommodates much more recoverable strain, reducing likelihood of a premature set in the wire (effectively rendering it useless until the next office visit).

The net effect of these improvements in wire performance seen with hyperelastic SMA archwires is a reduction in the quantity of wires required in series for clinical treatment with traditional NiTi wires. Chair time (frequency of visits) and overall case length may be diminished significantly. For example, a CuAlNi (or other hyperelastic SMA variants) archwire may reduce a traditional six wire sequence to a four or three wire case, resulting in cost and time savings to the patient and treating orthodontist.

DETAILED DESCRIPTION

The methods described herein are illustrated in the context of dental arch wires, however it should be understood that these methods are not limited to this use. In particular, the methods described herein may be used to set the shape of any shape memory alloy (SMA) material, particularly single crystal shape-memory alloy materials.

For convenience of use, straight wires are formed into an arch shape that approximately conforms to the shape of the jaw of the patient, a process known as shape-setting. NiTi based alloy wires are typically shape-set by winding on a mandrel having the desired arch shape, annealing by heating in a furnace to 400° C. or higher, and allowing the shaped wires to cool. This shape-setting process may take an hour or more.

The known and commercially used process described for shape-setting NiTi based wire cannot be used for shape-setting hyperelastic wire. Hyperelastic wire, typically single crystal, is not thermodynamically stable. At elevated temperatures of several hundred degrees, one or more of the components (especially Al) gradually forms precipitates. These precipitates remove the element from the crystal lattice, effectively changing the composition and hence the transition temperature of the alloy. A single crystal SMA wire heated to 500° C. and cooled over a period of several minutes has no shape memory and no superelasticity.

This effect, precipitation of Al, can be avoided if the wire is heated and cooled rapidly, for example in a few seconds. However, it is impractical to quickly heat and cool a mandrel of mass sufficient to impart the desired shape. This has led to the invention of the novel process for shape-setting hyperelastic wires for orthodontic arches described herein.

The present invention describes methods and processes for imparting an arch shape to a straight hyperelastic wire while preserving its elasticity and transition temperature. In particular, the method by which the heated wire is forced to take the shape of the shaping form (e.g., mandrel) without destroying the single-crystal properties is novel.

Figure 3:
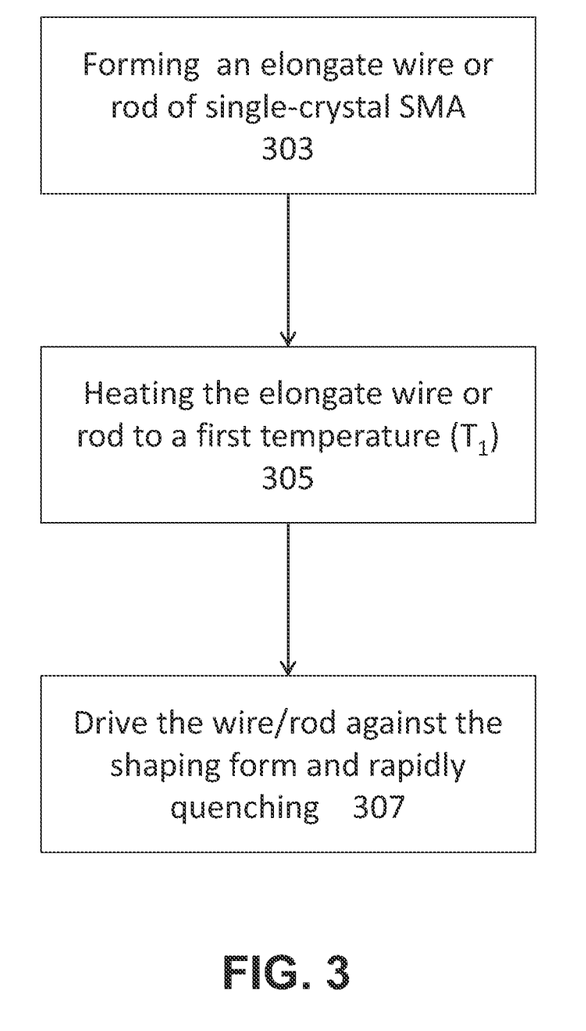
FIG. 3 is a diagram illustrating one method of forming an archwire.

In general, this method may include the steps of taking a single crystal SMA material (e.g., initially formed into an elongate member such as a wire or rod), heating the material to an annealing temperature ($T_a$) and quickly, if not simultaneously or near-simultaneously, driving the material around a shaping form (e.g., mandrel) and quenching it. FIG. 3 illustrates the various steps of this method including forming 303, heating 305 and shaping/quenching 307; each of these steps is described in greater detail and illustrated below.

A shaping form may also be referred to as a "form" or a mandrel, and is typically an object used to shape the hyperelastic single crystal material so that it may be simultaneously or virtually simultaneously quenched. Throughout this description, the shaping form may be referred to for convenience as a mandrel, but it should be understood that the shaping form may be any appropriate structure against which the heated SMA material may be driven to form-set the SMA material. The shaping form (e.g., mandrel) may be adapted so that the single crystal material can be driven against it with sufficient force to shape the single crystal material. The shaping form may also be adapted for movement with the shaped single crystal material into the quenching medium (e.g., bath). Some variations of a shaping form include dies or shaping apertures through which the single crystal material is drawn or forced as it is driven against the shaping form and into the quenching medium. A shaping for may be a thin element, which may be rapidly cooled/heated to aid in uniform quenching; in some variations the shaping form may be formed of a material having sufficient strength to support the single crystal material as it is driven against the shaping form, and also sufficient thermal conductivity to allow rapid, nearly uniform or uniform quenching.

A single crystal SMA may be initially formed by any appropriate method. Hyperelastic SMAs formed as single crystals, for example, single crystals of approximately Cu(81.2)Al(14.3)Ni(4.5) wt. percent may be formed as extruded shapes, whether by pulling from melt or by continuous casting. As mentioned above, although it is desirable to form other shapes, such as helices or bends, the methodology used for forming polycrystalline SMAs (e.g., Nitinol) destroys the single crystallinity; polycrystalline CuAlNi is brittle.

In general, any appropriate hyperelastic material may be used with the methods and systems described herein. For example, hyperelastic SMA materials that may be used include single crystal copper-based shape memory alloys such as: CuAlNi, CuNiMn, CuAlBe, and CuAlNiMnTi. In particular, single-crystal SMAs that may useful include CuAl (14-14.5%)Ni(3-4.5%); CuAl(12%)Be (0.5%); and CuAl (12%)Ni(4%)Mn(2%)Ti(1%).

The fabrication and performance of such single crystal SMA materials are disclosed, for example, in U.S. patent application Ser. No. 10/588,412 filed Jul. 31, 2006, the disclosure of which is incorporated by this reference. For example, single crystal CuAlNi may be drawn from melt and cooled by use of the Stepanov method. As the single crystal cools, precipitates may form so that strength, shape memory, and hyperelastic properties are not optimal. Imparting shape memory and hyperelastic properties requires heating to a temperature high enough to dissolve the precipitates, followed immediately by rapid cooling ("quenching") to lock in the dissolved elemental components. The use of elevated temperature to modify the shape of hyperelastic single crystal of CuAlNi normally results in loss of single crystallinity: at elevated temperatures precipitation of elemental components (especially Al) changes the composition. For this reason actuators and flexures designed to exploit the extraordinary strain recovery of these materials (>10% strain) have been limited to net shapes solid and tubular cylinders) produced during formation of the crystal.

CuAlNi single crystal is in a metastable condition and gradually deteriorates to polycrystalline form. The rate of decomposition is temperature dependent. At room temperature the rate is sufficiently low that negligible change takes place over years. At 300-400° C., the rate is rapid enough that degeneration to multiple crystals may occur in a few seconds. Once formed, the multiple crystals do not re-form as a single crystal: this requires melting and special processing. However, CuAlNi may retain its single crystal condition through repeated heating to annealing temperature and rapid cooling. At sufficiently high temperature (typically 850-950° C.) the three components Cu, Al, and Ni are in solution. CuAlNi's hyperelastic properties are exhibited within a very narrow range of compositions. If cooling is not sufficiently rapid, Al precipitates form, changing the composition and drastically altering thermo-mechanical properties. This effect was described, for example, in U.S. Pat. No. 7,842,143 to Johnson.

Returning to FIG. 3, the heating step 305 may be performed quickly. In some variations, the wire is heated by Joule heating, either as an electrical pulse or as a continuous electrical current, AC or DC, to annealing temperature. Copper-based single crystal alloys are good conductors, having resistivity about 8 micro-ohm cm. Hence it is essential to match the electrical impedance of the electrical power supply to the load by providing a low-voltage, high-current source. Voltage applied to the wire ends is typically 1 to 3 volts. Typical currents are from 10 to 30 amperes. The wire may be heated to its annealing temperature ($T_a$). In general, the annealing temperature is greater than about 600° C. (e.g., approximately between about 600° C. and 900° C.). For example, suitable annealing temperatures may range from 650 to 850 degrees C. This temperature may be estimated by its bright red color or measured by infrared thermometer.

While the single crystal material is at annealing temperature, the wire is quickly (e.g., within less than 0.5 seconds) wrapped about a shaping form having the desired arch shape, then plunged into a quenching bath 307. The full sequence of heating, forcing the shape, and cooling may take less than a second (or less than a few seconds).

In general, an apparatus or device for shape-setting a single crystal shape memory alloy without degrading the hyperelastic properties may include a heating feature (e.g., a resistive heating control for applying electrical energy to heat the single crystal material, a furnace element, etc.), a shaping form for forming the shape (which may include a mold, cut aperture, or the like), a quenching bath for quenching/cooling the shaped material, and a driver for driving the single crystal material against the shaping form and into the quenching bath.

Figure 2:
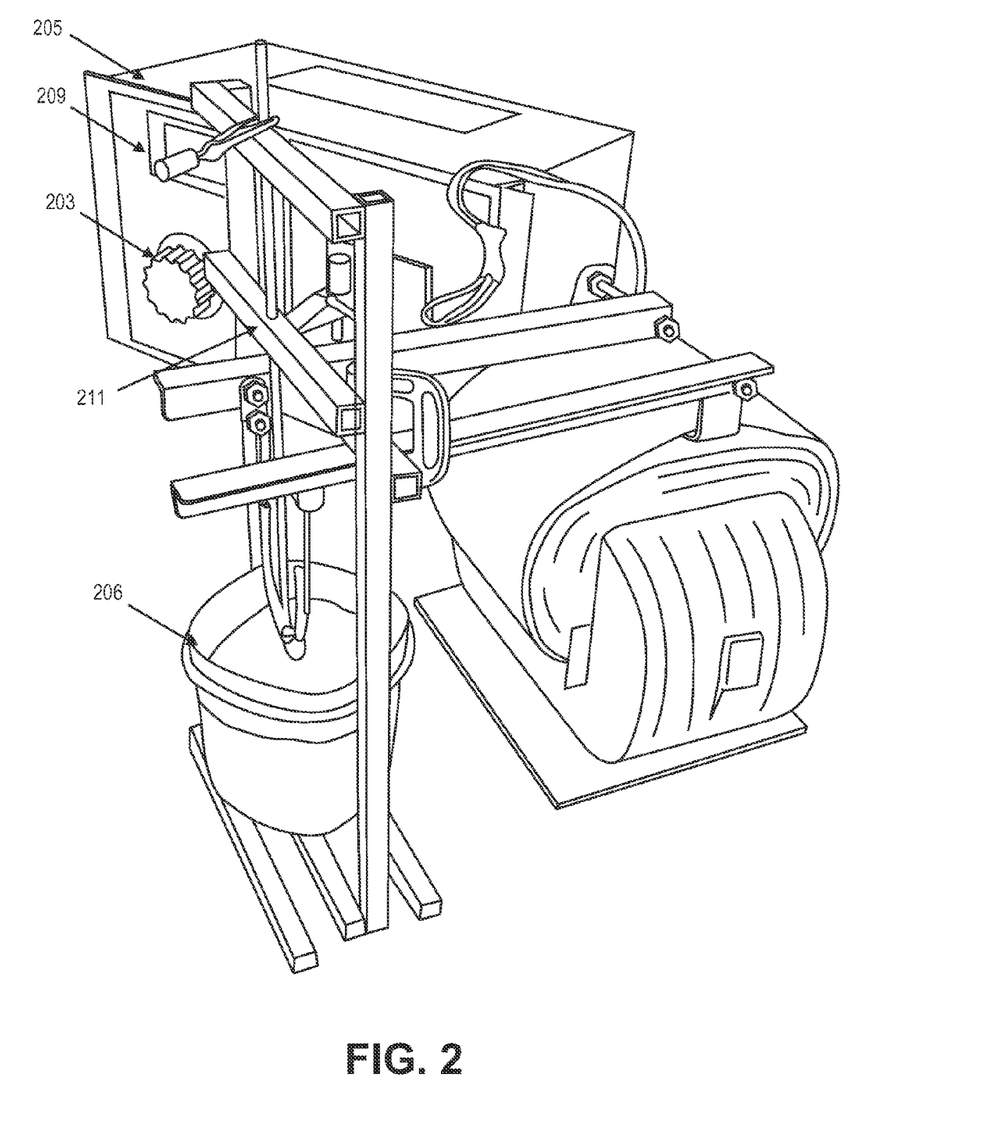
FIG. 2 illustrates one variation of a device for forming an archwire.

For example, FIG. 2 illustrates one variation of an apparatus for shape-setting hyperelastic wires, in this first embodiment of the device for shape-setting or forming an archwire of single crystal, hyperelastic material, an apparatus may consist of a variable voltage transformer 205, a quench bath 206, clamps or tubes that hold the wire ends in contact with the output (low-voltage) electrodes 209 of the transformer, and a plunger 211 with a U-shaped concavo-convex metal (copper) mandrel 215.

In FIG. 2, the device includes a variac whose control knob 203 (at the left side of the illustration) supplies a stepped down voltage to the power transformer at center right in the photograph. This transformer further steps down the AC voltage to a range of 1-3 volts, supplying a current of 10-40 amperes to the electrodes. These electrodes are two brass bars, suspended on a translucent plastic frame, extending from the power transformer electrical terminals to the hyperelastic wire. A portion of the hyperelastic wire may be seen below the forming mandrel, a U-shaped metal trough with flanges extending outward. The mandrel is prevented from falling onto the wire by a rod attached at the center of the U, extending through the translucent plastic frame and held temporarily by a clamp. The process consists of heating the wire by current from the electrodes until it is annealed (greater than about 600° C.), then releasing (un-clamping) the forming mandrel with attached rod so that it falls onto the wire, forming the wire about the mandrel, disconnecting it from the electrodes, and forcing it into the vessel of quenching water. The heating process can be accomplished in less than 5 seconds: quenching takes place in a few milliseconds.

In this variation, the driver driving the mandrel and SMA into the quench medium is the framework that drops the heated single crystal, hyperelastic SMA material against the mandrel and into the quench medium. The framework includes a plunger that is moved by gravity so that, upon release, the heated SMA is dropped against the mandrel (or the mandrel is driven against the heated SMA material) and into the quench bath, so that shaping by the mandrel and quenching occurs virtually simultaneously (e.g., with a few seconds or faster).

Any appropriate driver may be used. For example, the driver does not have to be gravity driven, but can be motorized, pneumatic, or otherwise moved to drive the heated SMA material against the mandrel and into the quench medium.

As mentioned above, any appropriate mandrel (form) may be used to shape the heated single crystal, hyperelastic SMA material. For example, in another variation, the mandrel is made of machined steel iii the form of a Damon Ormco archwire, Part Number 205-1903. The mandrel is attached to a linear ball bearing manufactured by W.M. Berg Inc. (499 Ocean Ave, E. Rockaway N.Y. 11518). In some variations the mandrel or form is modified or destroyed by the shaping process. For example, the mandrel may be single-use or frangible. In some variations the mandrel may be durable and reusable.

in the example shown in FIG. 2, electrical power for Joule heating is controlled by a foot-operated switch that also operates a solenoid-powered latch, providing improved timing control of the quenching operation. Other controls for the forming device/apparatus may be used. In some variations it may be beneficial to have a single trigger or control that activates the heating/driving/quenching method, since the entire process is so rapid and coordinated.

In general, the form/mandrel and the heated SMA material may be driven together and into the quench medium with force. The amount of force may be relatively low (e.g., the force applied by the weight of the archwire falling onto the form/mandrel), or high. The force may be adjustable or controlled by the driver.

In some variations, the temperature of the wire can be sensed by an infrared sensor. The heated wire can be formed around the mandrel, which may then take a wide variety of shapes, prior to quenching. Rapid cooling can be provided by a pulse of cold gas such as nitrogen from liquefied $N_2$.

In any of the variations, the material may be quickly heated to the annealing temperature, and forcibly contacted with the mandrel and quenched nearly immediately upon reaching the annealing temperature. Thus, the rate at which the temperature of the single crystal SMA material is heated may be controlled so that it is heated quickly (e.g., less than a second) and upon reaching the desired temperature, the shaping/quenching step may be performed immediately and rapidly.

In some of the examples provided herein, the mandrel may be suspended above the wire until the wire is heated to the desired temperature ($T_a$); then the mandrel is released so that it falls by gravity (or by other or additional mechanical force such as a spring, motor, etc.), against the heated wire. The force exerted on the wire by the mandrel as it falls pulls the wires from the clamps or tubes: this pulling force ensures that the wire is constrained to align with the inner groove shape of the mandrel. The mandrel immediately begins to absorb heat from the wire by contact, and both the mandrel and the wire are quickly cooled by immersion in a water bath, preferably a saltwater bath.

The mandrel in the example of FIG. 2 is made of a single sheet of copper, e.g., thickness 0.005-0.020 inches, approximately 7 inches long and 0.5 inches wide. This sheet is folded along its long axis while being bent along the apex into a desired U shape with the edges pointed outward from the fold. This complex bend can be accomplished by lightly hammering the folded copper sheet into the desired U shape, with repeated annealing at a high enough temperature that the copper does not become work hardened. This technique is well known to metal art workers.

Figure 1A:
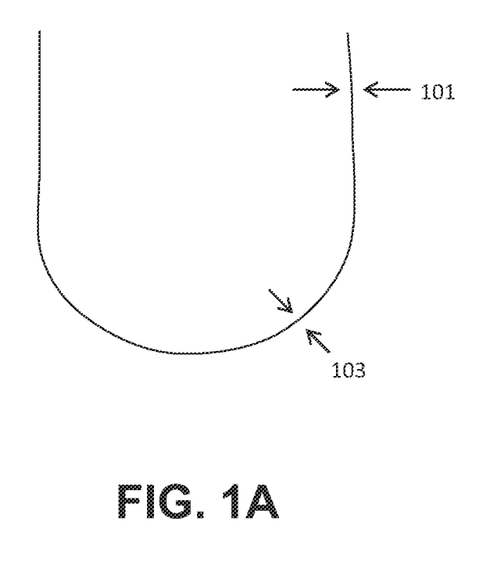
FIG. 1A shows one example of an archwire.

Returning now to FIGS. 1A-1D, these figures illustrate various embodiments of archwires which may be formed by the methods described herein. For example, FIG. 1A shows a schematic of an orthodontic archwire. In this example, the archwire is a single crystal SMA wire, approximately 0.016 inches in diameter, formed into an arch shape as described above. The archwire form is approximately three inches high and three inches wide.

Figure 1B:
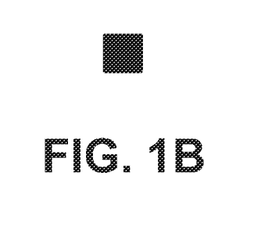
FIGS. 1B-1D shows exemplary cross-sections through an archwire such as the one shown in FIG. 1A.
Figure 1C:
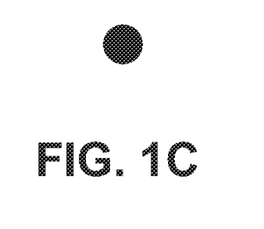
Figure 1D:
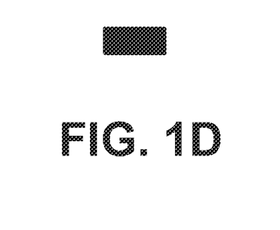

FIGS. 1B to 1C illustrate various cross-sections of such an archwire. For example, FIG. 1B shows a round (or ovoid) cross-section. FIG. 1C shows a square cross-section, while FIG. 1D shows a rectangular cross-section. In any of these examples, the entire archwire may have the same cross-sectional shape and/or diameter, or different regions of the archwire may have different cross-sectional shapes and/or diameters. For example, in some variations the archwire may have a round cross-section in some regions (e.g., 103) and a rectangular cross-section in other regions (e.g., 101). In some variations the different regions of the archwire 101, 103 may have different properties based on the composition and treatment of that region of the single crystal SMA.

In general, rectangular archwires may be made using the method and devices described above. For example, a rectangular archwire may be made using a mandrel configured to include a die through which (or against which) the heated wire is quickly drawn or forced; additional shaping (e.g., adding a curve) may be performed simultaneously.

Archwires having rectangular cross-sections (or rectangular over a portion of the length of the archwire) may be desirable because they may allow an orthodontist applying the archwire an additional degree of freedom when manipulating the teeth.

In some variations the same single crystals, hyperelastic material may be shaped multiple times to form a final shape. For example, an archwire may be formed into a rectangular wire in a first round of processing, and then shaped into the curved shape in a second round of processing; each round may include heating the material to the appropriate annealing temperature, then forcing it against (or being forced against) a mandrel near-simultaneously with quenching.

SUMMARY

As discussed above, hyperelastic materials have desirable characteristics (including operation at lower forces, recovering fully from distortions, and the like). However, fabrication methods adequate for the treatment of Nitinol (e.g., winding on a mandrel, then heating in an oven, removing the oxide layer, and cutting) can not readily be performed to single crystal materials without damaging them. For example, if such materials are maintained at a high (shape setting) temperature for very long, or cool slowly, the shape memory characteristics change drastically. It has proven difficult to shape-set single crystal materials.

As described herein, we have found that if the material is heated and cooled quickly (and particularly cooled quickly), all of the elemental components may be kept in solution: quenching leaves the effective composition unchanged because no significant amount of precipitation (e.g., Al precipitation) takes place. As described herein, Joule heating by means of a low-voltage, high-current electrical current to quickly heat the wire to annealing temperature quickly, then simultaneously or virtually simultaneously quenching and shaping the material, cooling it very rapidly, allows the single crystal material to be shape-set without diminishing the material properties. Thus, as described herein, shape setting of single crystal material may be performed by heating the material to the appropriate temperature, then shaping and quenching it by driving it into water while forming it into the desired shape (e.g., against the form/mandrel) within fraction of second. Forming and cooling are virtually simultaneous.

Although described herein as particularly useful in forming hyperelastic SMA materials into archwires, the method of shape-setting described herein may also be used to any shape any wire material that it is desired to form into a simple curve, including polycrystalline SMA materials such as titanium-nickel based alloys that are commonly used for archwires. Thus, the techniques described herein may be necessary to shape-set single crystal materials, but the techniques may also be adapted to shape-set ternary titanium alloys and other metallic conducting alloys as well, faster and using less energy than existing methods.

Further, the methods described herein are particularly well-suited to automation, as any (or all) of these steps may be automated. In contrast, conventional methods, e.g., winding on mandrel, tying the ends down, putting into an oven, cutting—are difficult to automate effectively.

Since polycrystalline SMAs have inferior properties compared to single crystal, hyperelastic, SMAs (particularly with respect to maintaining equal loading and unloading stress at very high strains), hyperelastic SMA material may be used to create archwires using the techniques described herein, and the resulting archwires may have superior properties. For example, hyperelastic alloy formed as described herein have been observed to exhibit excellent properties in wire form, ideally fitting archwire use in traditional orthodontics. For example, these materials may exhibit profound "superelasticity." The hyperelastic alloy crystal may be grown from melt through the (001) crystal plane, providing corresponding axis with maximum strain accommodation. In tension, >10% fully recoverable strain is achieved with no residual effect. In single crystal, the full potential of the crystal structure is used during the Stress Induced Martensite (SIM), defined as $\beta_1 \rightarrow \beta_1'$. SMA's are elastically hindered by grain boundaries, anisotropic texture (crystal orientation), dislocations and process inconsistencies. NiTi wires for orthodontic use generally achieve 4-6% recoverable strain. Once the crystal is grown in these hyperelastic alloys, mechanical properties are essentially locked into the structure. The critical stress for slip ($\sigma_c$) is extremely high, inhibiting the introduction of dislocations in the crystal.

Further, the single crystal SMAs described herein are biocompatible. This biocompatibility may be a result of the Cu and Al in these ternary compositions, which may provide a surface oxidation opportunity for the alloy, enabling protection from corrosive environments such as body fluids and specifically saliva. These $CuO$, $Cu_2O$, $Cr_2O_3$, and $Al_2O_3$ layers are submicron thick, demonstrating excellent resistance to in vitro pH cycling in a representative case of oral activity. The CuAlNi alloys examined have thus far exhibited no cytotoxicity, systemic toxicity, genotoxicity, implantation effects and are completely hemocompatible (reference ISO standard 109931).

The single crystal SMAs described herein also do not exhibit stress hysteresis. In tension, hyperelastic alloys have demonstrated negligible stress hysteresis when strained to 10%. Loading and unloading curves in an S-S diagram effectively overlap. In addition, these hyperelastic SMAs exhibit a low constant force. The lack of a stress hysteresis guarantees consistent force application upon the return path for any induced load. However, an additional key feature of hyperelastic alloys is a constant force expression from the material along that path regardless of strain. This constant plateau force is considerably lower than that of traditional NiTi alloys, which sometimes express forces proportionally to rising strain (not constant). In orthodontic applications, this means a larger cross-section hyperelastic wire behaves likes a much smaller NiTi wire. The plateau height can be precisely set by material chemistry (e.g. Al wt % is inversely proportional to $A_f$ temp) and anneal/quench processes.

Figure 4:
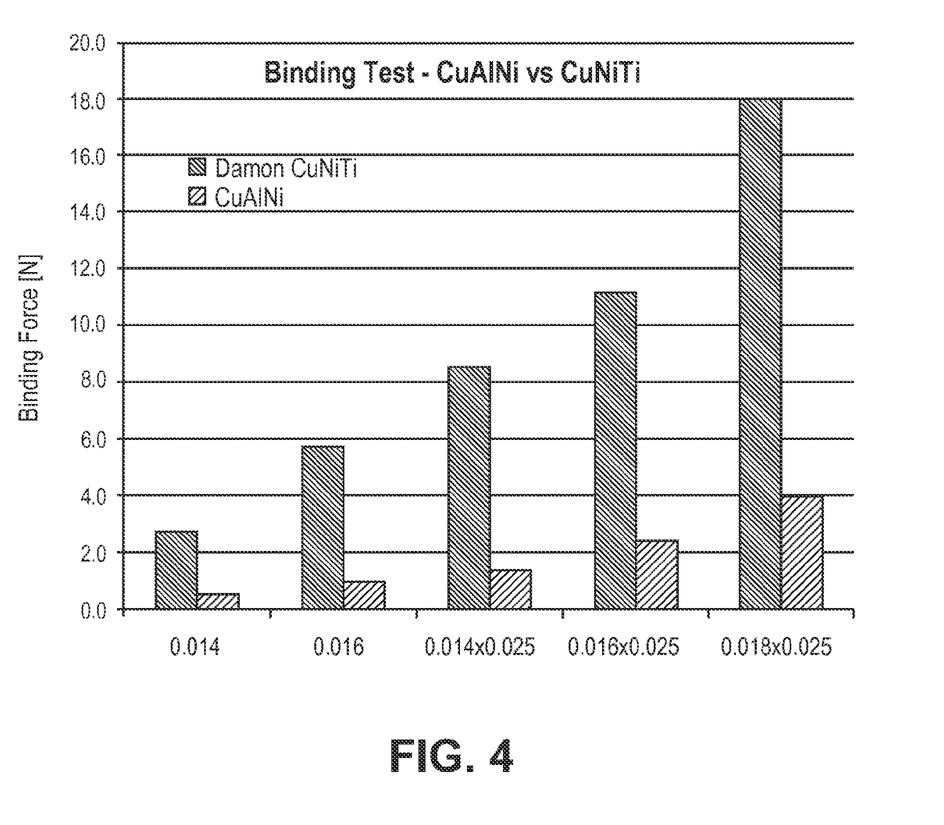
FIG. 4 is a graph of the results of a binding test comparing a polycrystalline SMA (CuNiTi) and a single crystal SMA material (CuAlNi).

In addition, the single crystal SMAs described herein exhibited significantly reduced orthodontic resistance to sliding; hyperelastic archwires formed of single crystal SMAs have much less binding and/or friction with standard brackets in vitro than traditional NiTi alloys. It is believed that normal force to the bracket body at the point of contact is the critical element in orthodontic sliding mechanics. When stressed about a corner, hyperelastic archwires preferentially transform locally to SIM rather than notch, bend or structurally dislocate. This enables the wire to better negotiate non-linearities in maloclussive ligation to the bracket, reducing the normal force. Less normal force effectively reduces opportunities for binding and friction. The oxide layer may also provide a hard, non-compliant surface, allowing the wire to negotiate corners more effectively, again reducing normal force. For CuAlNi, preliminary testing suggests a commercially electropolished surface reduces orthodontic resistance to sliding (binding) by ~80% in comparison to traditional NiTi wires. For example, see FIG. 4.

Finally, the single crystal SMAs described herein may also have a superior fatigue life. For example, cantilever fatigue testing of CuAlNi demonstrates a 2-3 times increase in cycle times to traditional NiTi Alloys.

Because of these advantages, hyperelastic archwires may potentially replace titanium-nickel-based archwires in a large percentage of orthodontic procedures.

Although many of the devices, systems and methods described above refer primarily to archwires for dental/orthopedic applications, shape-set hyperelastic SMA structures may be useful for a variety of applications and may thus be formed into a variety of shapes. For example, hyperelastic SMA structures may be used for other applications, including other dental applications. Other structures that may be formed as described herein (and thus may be formed out of single crystal, hyperelastic SMA materials) may include: Herbst appliances (e.g.; U.S. Pat. No. 5,645,423); retraction arch (U.S. Pub. No. 2010/0129766 A1); temporary attachment device accessories (e.g., U.S. 2010/0190127); archwire ligating springs (e.g., U.S. Pat. No. 6,042,374); transpalatal expanders (e.g., U.S. Pat. No. 5,312,247); wire support embedded in aligners (e.g., see FIG. 2 of U.S. 2002/0192617); coil springs; and face bows. For example; the use of this material as part of a transpalatal expander could eliminate the need for patient compliance in periodically adjusting a screw. The slow and steady force used to expand the maxilla would come from steady forces.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the invention.

What is claimed is:

1. A method of shape-setting a hyperelastic material while preserving the hyperelastic properties of the material, the method comprising:
heating a single crystal shape memory alloy material to an annealing temperature $T_a$; and
driving the single crystal shape memory alloy material at the annealing temperature and a shaping form together into contact with each other and into a quenching medium;
wherein the heating and driving steps are performed in less than 10 seconds.

2. The method of claim 1, wherein heating comprises heating a wire or rod of single crystal shape memory alloy to the annealing temperature.

3. The method of claim 1, wherein heating comprises heating a wire or rod of single crystal shape memory alloy of CuAlNi, CuAlMn, or CuAlBe.

4. The method of claim 1, wherein heating comprises Joule heating a wire or rod of single crystal shape memory alloy.

5. The method of claim 1, wherein heating comprises heating within less than about 0.5 seconds.

6. The method of claim 1, wherein driving comprises driving the single crystal shape memory alloy material at the annealing temperature against the shaping form.

7. The method of claim 1, wherein driving comprises driving the shaping form against the single crystal shape memory alloy material at the annealing temperature.

8. The method of claim 1, wherein driving comprises colliding the single crystal shape memory alloy with a shaping form comprising a mandrel.

9. The method of claim 1, wherein driving comprises dropping the single crystal shape memory alloy material at the annealing temperature against the shaping form and into the quenching medium.

10. The method of claim 1, wherein driving comprises dropping the shaping form against the single crystal shape memory alloy material at the annealing temperature and into the quenching medium.

11. The method of claim 1, wherein driving comprises mechanically accelerating the single crystal shape memory alloy at the annealing temperature and the shaping form against each other and into the quenching medium.

12. The method of claim 1, wherein driving comprises quenching the single crystal shape memory alloy in the quenching medium comprising salt water.

13. The method of claim 1, wherein the heating and driving steps are performed in less than a few seconds.

14. The method of claim 1, wherein the heating and driving steps are performed in less than a second.

15. The method of claim 1, wherein the step of driving comprises forming a dental archwire from the single-crystal shape memory alloy by driving the single crystal shape memory alloy material at the annealing temperature and the shaping form together and into the quenching medium.

16. A method of shape-setting a hyperelastic material into a dental archwire while preserving the hyperelastic properties of the material, the method comprising:

heating a wire of single crystal shape memory alloy material to an annealing temperature ($T_a$); and driving the wire at the annealing temperature and a shaping form together into contact with each other and into a quenching medium to shape-set the wire into an archwire shape;

wherein the heating and driving steps are performed in less than five seconds.

17. The method of claim 16, wherein heating comprises heating the wire, the wire comprising a single crystal shape memory alloy of CuAlNi, CuAlMn, CuAlBe, or CuAlNiMnTi.

18. The method of claim 16, wherein heating comprises Joule heating the wire of single crystal shape memory alloy.

19. The method of claim 16, wherein heating comprises heating within less than about 0.5 seconds.

20. The method of claim 16, wherein driving comprises driving the wire at the annealing temperature against the shaping form.

21. The method of claim 16, wherein driving comprises driving the shaping form against the wire at the annealing temperature.

22. The method of claim 16, wherein driving comprises colliding the wire at the annealing temperature with a shaping form comprising a mandrel.

23. The method of claim 16, wherein driving comprises dropping the wire at the annealing temperature against the shaping form and into the quenching medium.

24. The method of claim 16, wherein driving comprises dropping the shaping form against the wire at the annealing temperature and into the quenching medium.

25. The method of claim 16, wherein driving comprises mechanically accelerating the wire at the annealing temperature and the shaping form against each other and into the quenching medium.

26. The method of claim 16, wherein driving comprises quenching the wire in the quenching medium comprising salt water.

27. The method of claim 16, wherein the heating and driving steps are performed in less than a second.

* * * * *